US009031665B2

(12) United States Patent
Aghassian (10) Patent No.: US 9,031,665 B2
(45) Date of Patent: May 12, 2015

(54) EXTERNAL CONTROLLER/CHARGER SYSTEM FOR AN IMPLANTABLE MEDICAL DEVICE CAPABLE OF AUTOMATICALLY PROVIDING DATA TELEMETRY THROUGH A CHARGING COIL DURING A CHARGING SESSION

(71) Applicant: Boston Scientific Neuromodulation Corporation, Valencia, CA (US)

(72) Inventor: Daniel Aghassian, Glendale, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 0 days.

(21) Appl. No.: 13/892,753

(22) Filed: May 13, 2013

(65) Prior Publication Data

US 2013/0245721 A1    Sep. 19, 2013

Related U.S. Application Data

(62) Division of application No. 12/616,250, filed on Nov. 11, 2009, now Pat. No. 8,463,392.

(51) Int. Cl.
*A61N 1/05*    (2006.01)
*A61N 1/378*    (2006.01)
*A61N 1/372*    (2006.01)

(52) U.S. Cl.
CPC ............ *A61N 1/3787* (2013.01); *A61N 1/37223* (2013.01); *A61N 1/37229* (2013.01)

(58) Field of Classification Search
USPC ........... 607/1–2, 16, 32, 60–61, 65, 115–116, 607/148; 343/718; 340/539.12
IPC .. A61B 5/0031; G06F 19/3406,19/3412; A61N 1/37, 1/00, 1/40; H02J 7/007, 7/025, 17/00; Y10S 128/903; A61F 2250/0002
See application file for complete search history.

(56) References Cited

U.S. PATENT DOCUMENTS

| | | |
|---|---|---|
| 4,561,443 A | 12/1985 | Hogrefe et al. |
| 6,516,227 B1 | 2/2003 | Meadows et al. |
| 7,177,698 B2 | 2/2007 | Klosterman et al. |
| 7,428,438 B2 | 9/2008 | Parramon et al. |
| 2003/0078634 A1 | 4/2003 | Schulman et al. |
| 2004/0098068 A1 | 5/2004 | Carbunaru et al. |
| 2005/0021108 A1 | 1/2005 | Klosterman et al. |
| 2007/0060979 A1* | 3/2007 | Strother et al. ................. 607/60 |
| 2007/0060980 A1 | 3/2007 | Strother et al. |
| 2008/0027513 A1 | 1/2008 | Carbunaru |
| 2009/0069869 A1 | 3/2009 | Stouffer et al. |
| 2009/0112291 A1 | 4/2009 | Wahlstrand et al. |
| 2009/0118796 A1 | 5/2009 | Chen et al. |
| 2010/0204756 A1 | 8/2010 | Aghassian |

* cited by examiner

*Primary Examiner* — Deborah Malamud
(74) *Attorney, Agent, or Firm* — Lewis & Reese, PLLC (57) ABSTRACT

An external controller/charger system for an implantable medical device is disclosed, in which the external controller/charger system provides automatic switching between telemetry and charging without any manual intervention by the patient. The external controller/charger system includes an external controller which houses a telemetry coil and an external charging coil coupled to the external controller. Normally, a charging session is carried out using the external charging coil, and a telemetry session is carried out using the telemetry coil. However, when a patient requests to carry out telemetry during a charging session, the external charging coil is used instead of the internal telemetry coil.

11 Claims, 8 Drawing Sheets

EXTERNAL CONTROLLER/CHARGER SYSTEM FOR AN IMPLANTABLE MEDICAL DEVICE CAPABLE OF AUTOMATICALLY PROVIDING DATA TELEMETRY THROUGH A CHARGING COIL DURING A CHARGING SESSION

CROSS REFERENCE TO RELATED APPLICATIONS

This is a divisional of U.S. patent application Ser. No. 12/616,250, filed Nov. 11, 2009, (now U.S. Pat. No. 8,463, 392, granted Jun. 11, 2013), to which priority is claimed and which is incorporated herein by reference.

FIELD OF THE INVENTION

The present invention relates to data telemetry and power transfer in an implantable medical device system.

BACKGROUND

Implantable stimulation devices are devices that generate and deliver electrical stimuli to body nerves and tissues for the therapy of various biological disorders, such as pacemakers to treat cardiac arrhythmia, defibrillators to treat cardiac fibrillation, cochlear stimulators to treat deafness, retinal stimulators to treat blindness, muscle stimulators to produce coordinated limb movement, spinal cord stimulators to treat chronic pain, cortical and deep brain stimulators to treat motor and psychological disorders, and other neural stimulators to treat urinary incontinence, sleep apnea, shoulder sublaxation, etc. The present invention may find applicability in all such applications, although the description that follows will generally focus on the use of the invention within a Spinal Cord Stimulation (SCS) system, such as that disclosed in U.S. Pat. No. 6,516,227.

Figures 1A, 1B:
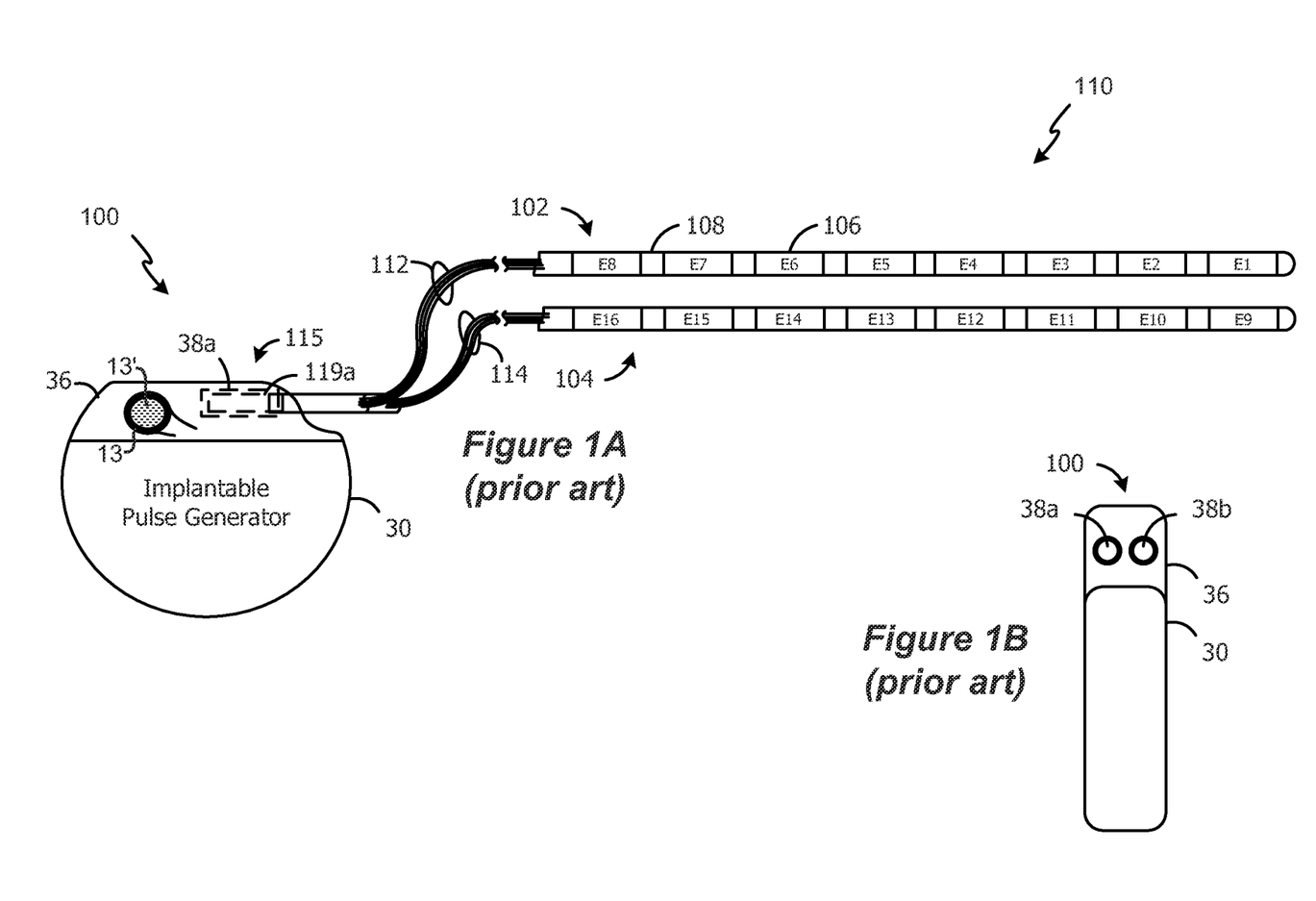
FIGS. 1A and 1B show an implantable pulse generator (IPG), and the manner in which an electrode array is coupled to the IPG in accordance with the prior art.

Spinal cord stimulation is a well-accepted clinical method for reducing pain in certain populations of patients. As shown in FIGS. 1A and 1B, a SCS system typically includes an Implantable Pulse Generator (IPG) 100, which includes a biocompatible case 30 formed of titanium for example. The case 30 typically holds the circuitry and power source or battery necessary for the IPG to function, although IPGs can also be powered via external RF energy and without a battery. The IPG 100 is coupled to electrodes 106 via one or more electrode leads (two such leads 102 and 104 are shown), such that the electrodes 106 form an electrode array 110. The electrodes 106 are carried on a flexible body 108, which also houses the individual signal wires 112 and 114 coupled to each electrode. In the illustrated embodiment, there are eight electrodes on lead 102, labeled $E_1$-$E_8$, and eight electrodes on lead 104, labeled $E_9$-$E_{16}$, although the number of leads and electrodes is application specific and therefore can vary.

Figure 2:
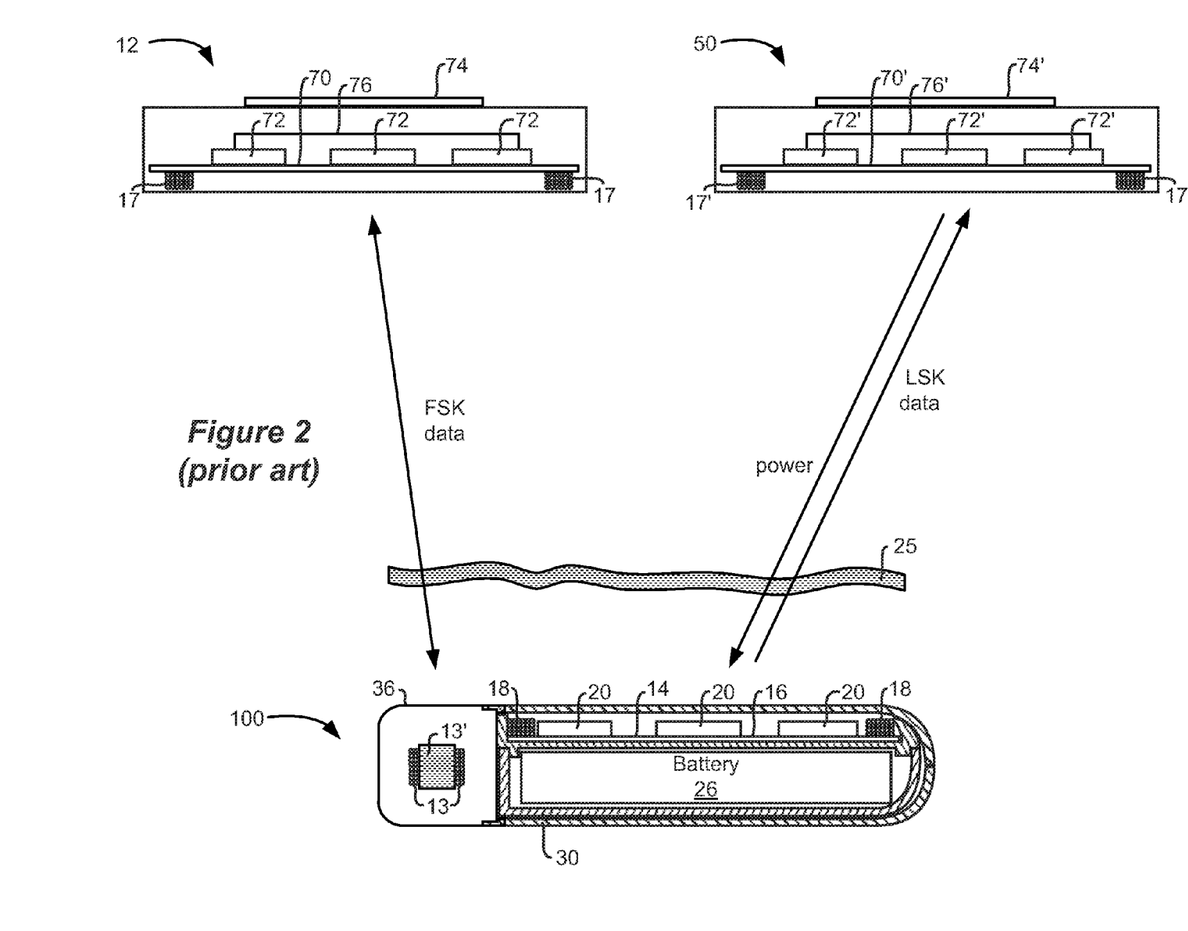
FIG. 2 shows wireless communication of data between an external controller and an IPG, and wireless communication of power from an external charger to the IPG in accordance with the prior art.

As shown in FIG. 2, the IPG 100 typically includes an electronic substrate assembly 14 including a printed circuit board (PCB) 16, along with various electronic components 20, such as microprocessors, integrated circuits, and capacitors mounted to the PCB 16. Two coils are generally present in the IPG 100: a data telemetry coil 13 used to transmit/receive data to/from an external controller 12; and a charging coil 18 for receiving power to charge the IPG's battery 26 using an external charger 50.

As just noted, an external controller 12, such as a hand-held programmer or a clinician's programmer, is used to wirelessly send data to and receive data from the IPG 100. For example, the external controller 12 can send programming data to the IPG 100 to dictate the therapy the IPG 100 will provide to the patient. Also, the external controller 12 can act as a receiver of data from the IPG 100, such as various data reporting on the IPG's status. The external controller 12, like the IPG 100, also contains a PCB 70 on which electronic components 72 are placed to control operation of the external controller 12. A user interface 74 similar to that used for a computer, cell phone, or other hand held electronic device, and including touchable buttons and a display for example, allows a patient or clinician to operate the external controller 12. The communication of data to and from the external controller 12 is enabled by a coil 17, which is discussed further below.

The external charger 50, also typically a hand-held device, is used to wirelessly convey power to the IPG 100, which power can be used to recharge the IPG's battery 26. The transfer of power from the external charger 50 is enabled by a coil 17', which is discussed further below. For the purpose of the basic explanation here, the external charger 50 is depicted as having a similar construction to the external controller 12, but in reality they will differ in accordance with their functionalities as one skilled in the art will appreciate.

Wireless data telemetry and power transfer between the external devices 12 and 50 and the IPG 100 takes place via magnetic inductive coupling. To implement such functionality, coils in the IPG 100 and the external devices 12 and 50 act together as a pair. In case of the external controller 12, the relevant pair of coils comprises coil 17 from the controller and coil 13 from the IPG. While in case of the external charger 50, the relevant pair of coils comprises coil 17' from the external charger and coil 18 from the IPG.

When data is to be sent from the external controller 12 to the IPG 100 for example, coil 17 is energized with an alternating current (AC). Such energizing of the coil 17 to transfer data can include modulation using a Frequency Shift Keying (FSK) protocol for example, such as disclosed in U.S. Patent Publication 2009/0024179. For example, FSK communication can be centered around 125 KHz for example, with 121 kHz representing a logic '0' and 129 kHz representing a logic '1'. Energizing the coil 17 produces a magnetic field, which in turn induces a current in the IPG's coil 13, which current can then be demodulated to recover the original data. Data telemetry in the opposite direction—from the IPG 100 to the external controller 12—occurs in essentially the same manner.

When power is to be transmitted from the external charger 50 to the IPG 100, coil 17' is again energized with an alternating current to produce a non-modulated magnetic charging field. Such energizing is generally of a constant frequency (e.g., 80 kHz), and may be of a larger magnitude than that used during the transfer of data, but otherwise the physics involved are similar.

During charging, i.e., when the external charger 50 is producing the magnetic charging field, the IPG 100 can communicate data back to the external controller using Load Shift Keying (LSK). LSK is well explained in U.S. Patent Publication 2010/0179618, and involves modulating the load at the IPG 100 to produce data-containing reflections detectable at the external charger 50. This means of transmitting data is useful to communicate data relevant during charging of the battery 26, such as whether charging is complete and the external charger 50 can cease production of the magnetic charging field. As one skilled in the art will understand, LSK data can only be communicated when the magnetic charging field is present, and can only be transmitted from the IPG 100 to the external controller 12. Moreover, LSK provides very low bit rates (e.g., 10 bits/second) and therefore the amount of data that can be sent by this means is limited.

Energy to energize coils 17 and 17' can come from batteries in the external controller 12 and the external charger 50, respectively, which like the IPG's battery 26 are preferably rechargeable. However, power may also come from plugging the external controller 12 or external charger 50 into a wall outlet plug (not shown), etc.

As is well known, inductive transmission of data or power can occur transcutaneously, i.e., through the patient's tissue 25, making it particularly useful in a medical implantable device system. During the transmission of data or power, the coils 17 and 13, or 17' and 18, preferably lie in planes that are parallel, along collinear axes, and with the coils as close as possible to each other. Such an orientation between the coils 17 and 13 will generally improve the coupling between them, but deviation from ideal orientations can still result in suitably reliable data or power transfer.

Although the external controller 12 and external charger 50 can be completely separate devices as shown in FIG. 2, other solutions have been proposed that integrate these two devices together to varying degrees. For example, in U.S. Patent Publication 2009/0118796, the circuitry for the external controller and the external charger are enclosed in a single housing. The coil for transferring data is enclosed within the housing, while the coil for transferring power to the IPG lies external to the housing, but is connected to the charging circuitry in the housing by a wire. In another solution disclosed in U.S. Pat. No. 8,335,569, the circuitry for the external controller and the external charger, and their associated coils, are enclosed within a single housing, which coils can be shared between the data telemetry and charging functions.

Even in these integrated controller/charger solutions, data transfer and power transfer do not take place at the same time. Therefore, if the patient needs to adjust the therapy program while the IPG is being charged for example, the patient is required to manually interrupt charging, manually activate the data telemetry circuitry, and then manually return to charging. The need to interrupt charging can occur in even simpler contexts such as if the patient merely wants to know the capacity of the battery while charging. Reporting of battery capacity in a manner reviewable by the patient is typically a data telemetry function under the control of external controller circuitry, and thus charging would need to cease to receive such data. Having to manually switch between charging and data telemetry functions is inconvenient for the patient. Not only may the patient need to manipulate a separate external controller and an external charger, the patient may also need to physically align those devices with the IPG to ensure good coupling between the coils in each of the devices. See, e.g., U.S. Pat. No. 8,473,066, discussing the importance of good coil alignment in this context. Such frustrations for the patient are especially needling when it is recognized that data telemetry may only take a short period of time (on the order of seconds or tenths of seconds) compared to the time needed the charge the IPG's battery (on the order of minutes or hours).

This disclosure provides embodiments of solutions to mitigate this problem.

DETAILED DESCRIPTION

The description that follows relates to use of the invention within a spinal cord stimulation (SCS) system. However, the invention is not so limited. Rather, the invention may be used with any type of implantable medical device system. For example, the present invention may be used as part of a system employing an implantable sensor, an implantable pump, a pacemaker, a defibrillator, a cochlear stimulator, a retinal stimulator, a stimulator configured to produce coordinated limb movement, a cortical and deep brain stimulator, or in any other neural stimulator configured to treat any of a variety of conditions.

An improved external controller/charger system for an implantable medical device is described herein, in which the external controller/charger system provides automatic switching between data telemetry and charging without any manual intervention by the patient. The external controller/charger system in one embodiment includes an external controller which houses a data telemetry coil and an external charging coil coupled to the external controller. Normally, a charging session is carried out using charging circuitry and the external charging coil, and a data telemetry session is carried out using data telemetry circuitry and the data telemetry coil. However, when a patient requests to carry out data telemetry during a charging session, the external charging coil is used instead of the internal data telemetry coil. Specifically, in one embodiment, the external controller/charger system automatically decouples the external charging coil from the charging circuitry and couples it to the data telemetry circuitry. The external charging coil is then tuned to function with the data telemetry circuitry if necessary. The device and the implantable medical device then carry out the desired data telemetry via the external charging coil. After a predetermined time, or after the data telemetry session is complete, the external controller/charger system automatically decouples the external coil from the data telemetry circuitry and recouples it to the charging circuitry, and if necessary retunes the external charging coil to once again function with the charging circuitry.

Thus, the improved external controller/charger system can automatically switch between data telemetry and charging without manual intervention from the patient. Moreover, because it can be assumed that the charging coil had been properly physically aligned for good coupling with the IPG during the charging session, data telemetry can automatically proceed through the charging coil without the need for the patient to further worry about such alignment issues, thus simplifying patient operation of the system. As a further benefit, because both the data telemetry coil and the charging coil in the external system are tuned to the same frequency and use the same communication protocol during telemetry, the data telemetry circuitry in the implant does not need to be changed to communicate with either of these external coils, and the implant can freely communicate without concern to which coil is presently active in the external system.

Figure 3:
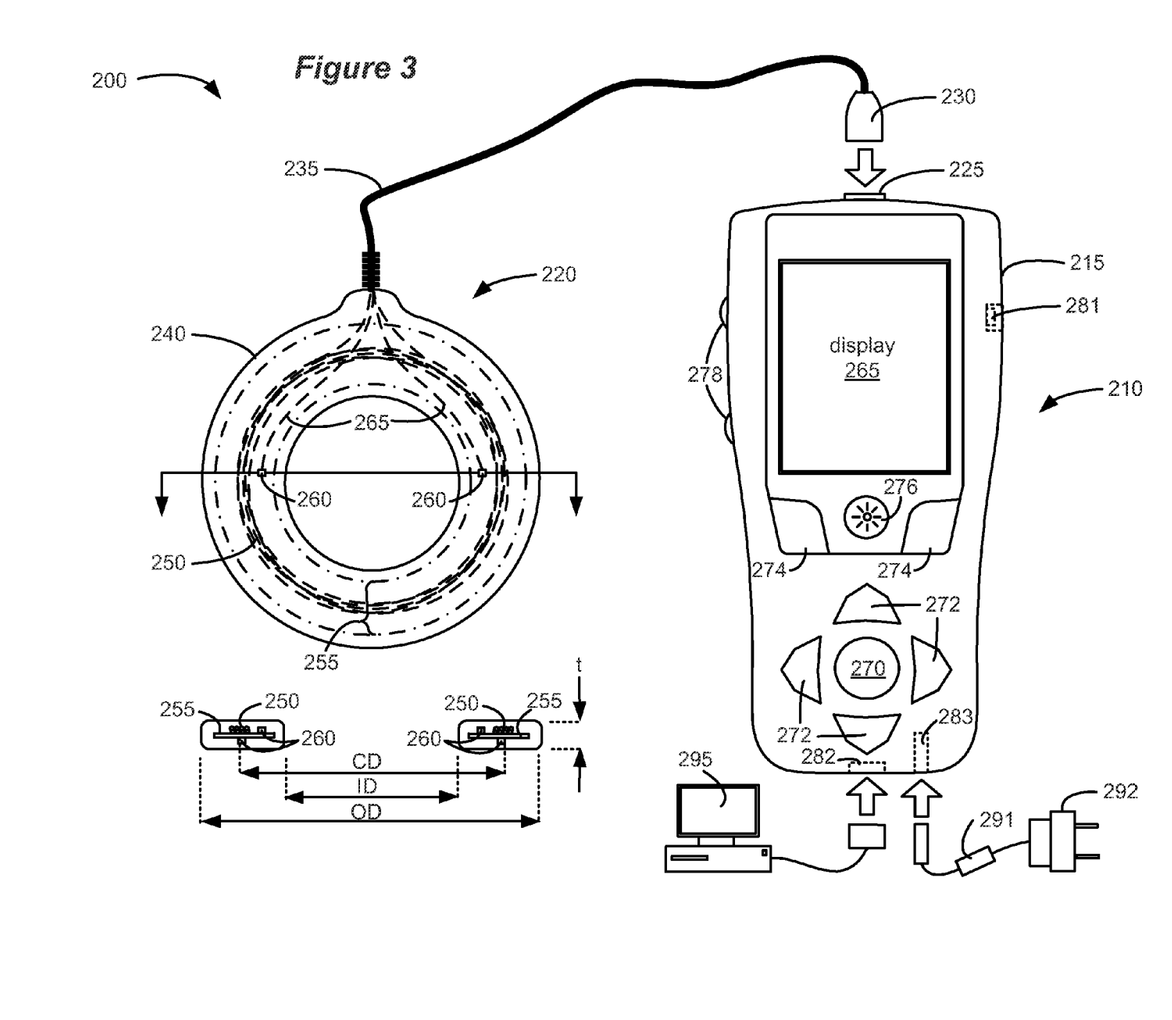
FIG. 3 shows an external controller/charger system in accordance with an embodiment of the invention comprising an external controller with a detachable external charging coil assembly.

One embodiment of the improved external controller/charger system 200 is shown in FIG. 3. Much of the basic structure of system 200 is disclosed in U.S. Patent Publication 2009/0118796, which is incorporated herein by reference. For completeness, some of the disclosure from the '796 Publication is set forth here before aspects of the improved data telemetry/charging functionality are discussed.

In system 200 the data telemetry and charging functionality are integrated. The system 200 includes an external controller 210 and an external charging coil assembly 220 that is coupled to the external controller 210. External controller 210, without the external charging coil assembly 220, can send and receive data telemetry to and from the IPG 100. Additionally, with the external charging coil assembly 220 connected, external controller 210 can send power to the IPG 100 via the external charging coil assembly 220. Furthermore, as discussed in detail below, the external controller 210 can send and receive data telemetry to and from the IPG 100 using the external charging coil assembly 220.

Housing 215 of the external controller 210 includes a port 225 into which a connector 230 of the external charging coil assembly 220 can be placed. The connector 230 is connected by a cable 235 to an external coil housing 240 portion of the assembly 220. The charging coil housing 240 contains a charging coil 250. In the depicted embodiment, the charging coil housing 240 is roughly donut shaped to accommodate the circular shape of the charging coil 250, but the shape can vary. For example, the charging coil housing 240 can be disc shaped and thus can lack a central hole.

The construction and inductance of charging coil 250 can vary depending on the circumstances. That being said, the coil diameter (CD) is preferably made large (for example, several centimeters) to maximize the reliability of coupling with the charging coil 18 and the data telemetry coil 13 in the IPG 100. External charging coil assembly 220 can include a substrate 255 for holding electronic components, such as the charging coil 250 and temperature-sensing thermistors 260.

External controller 210 integrates data telemetry and charging functionality via its microcontroller 402 (see FIG. 5), and provides the user access to such functionality through a single user interface. The user interface generally allows the user to telemeter data (such as a new or adjusted therapy program) from the external controller 210 to the IPG 100, to charge the battery 26 in the IPG 100, or to monitor various forms of status feedback from the IPG 100 such as IPG battery capacity. The user interface includes a display 265, an enter or select button 270, and menu navigation buttons 272 and 274. Soft keys 278 can be used to select various functions, which will vary depending on the status of the menu options available at any given time.

The display 265 optimally displays both text and graphics to convey necessary information to the patient such as menu options, stimulation settings, IPG battery status, external controller battery status, to indicate if stimulation is on or off, or to indicate the status of charging. Display 265 can be constructed using various display technologies, and can also include a touch sensitive overlay that provides an interface in addition to the buttons 270 and 272. A speaker can also included within the housing 215 to provide audio cues to the user (not shown). Alternatively, a vibration motor can provide tactile feedback.

External controller 210 can also include a battery for powering its operations. Such battery can comprise a standard disposable alkaline battery, a Lithium-ion battery, a Lithium-polymer battery, etc., or other types of rechargeable batteries. Alternatively, power can be provided by an external power source connected to the power port 283. Such a power source can include an adapter 291, which converts AC voltage drawn from a AC power source (e.g., wall outlet) via a wall plug 292 to the appropriate DC voltage. The external power received at the power port 283 can also be used to recharge batteries in the external controller 210.

A data port 282 can be provided to allow the external controller 210 to communicate with other devices such as a computer 295. Such a data port 282 is useful to share data with another machine, to allow the external controller 210 to receive software updates, or to allow the external programmer 210 to receive a starter therapy program from a clinician programmer. Port 282 can also comprise a wireless IRDA port. Alternatively wireless communication to and from the external controller 210 can occur using a short-range communication protocol such as Bluetooth, as disclosed in U.S. Patent Publication 2010/0305663.

With a basic description of the improved external controller/charger system 200 in hand, attention turns to a discussion of how system 200 improves the interplay between charging and data telemetry.

Figure 4:
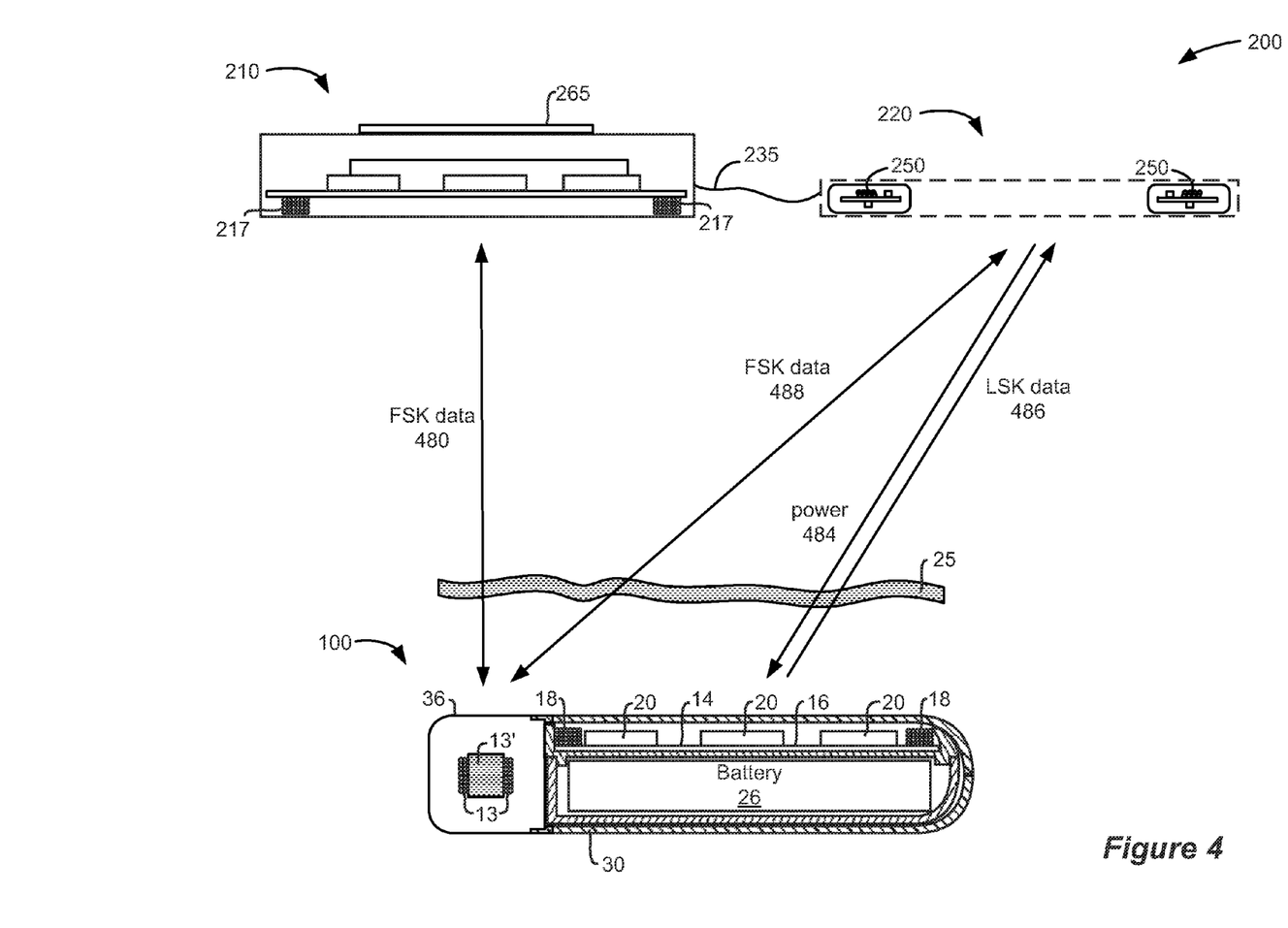
FIG. 4 shows wireless power transmission and data telemetry between the detachable external charging coil and the IPG in accordance with an embodiment of the invention.

FIG. 4 shows the improved external controller/charger system 200 in cross section and in conjunction with an IPG 100, and shows the various communication links between them. As shown, the external controller 210 can bi-directionally communicate data 480 with the IPG 100, with such communication taking place between data telemetry coils 217 and 13 in the external controller 210 and the IPG 100 respectively. Data 480 can be encoded according to an FSK protocol, as mentioned earlier. Power 484 can be conveyed from the charging coil 250 in the external charging coil assembly 220 to the charging coil 18 in the IPG 100, as was discussed in the above-reference '796 application. Additionally, and novel to this disclosure, the charging coil 250 can bi-directionally communicate data 488 with the data telemetry coil 13 in the IPG 100 during a charging session. Data 488, like data 480, can be encoded according to an FSK protocol, although this is not strictly necessary.

Figure 5:
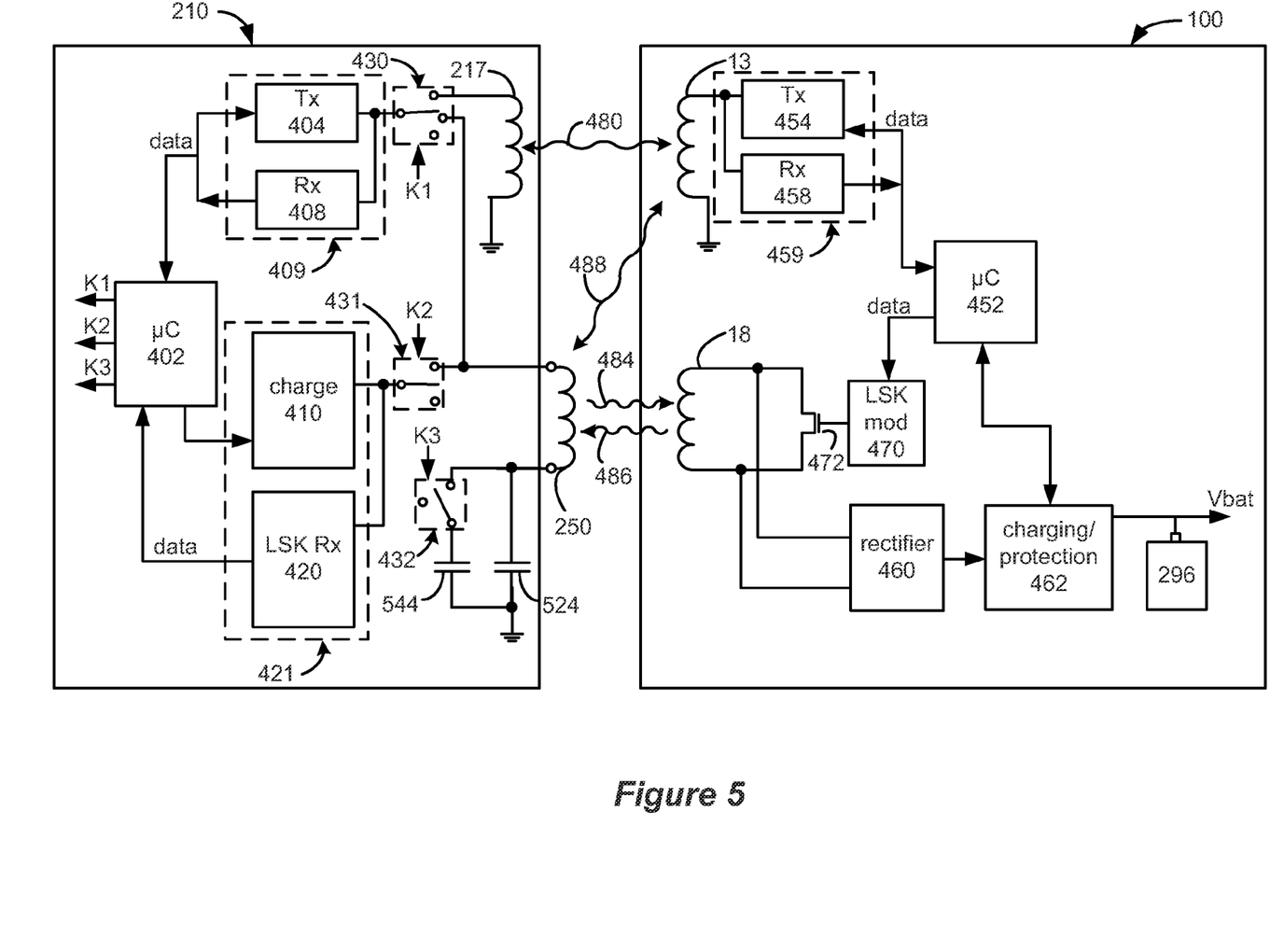
FIG. 5 shows a schematic of the circuitry in the external controller/charger system and in the IPG in accordance with an embodiment of the invention.

FIG. 5 shows communication circuitry within the external controller 210 and the IPG 100 for enabling the various communication links just described. External controller 210 includes data telemetry circuitry 409 comprising transmitter circuitry 404 and receiver circuitry 408 for transmitting and receiving data to and from the IPG 100. The transmitter circuit 404 includes modulation circuitry and amplifiers that drive either the data telemetry coil 217 or the charging coil 250 with an alternating current to transmit modulated data. The alternating current generates a magnetic field comprising data 480 (from the data telemetry coil) or 488 (from the charging coil 250), which, in turn, induces a current in the IPG's 100 data telemetry coil 13. Data telemetry coils 217 and 13 can be permanently tuned to a center frequency of 125 KHz enabling FSK communications as discussed earlier. The charging coil 250 can be temporarily tuned to this same frequency, as discussed further below. The data received at data telemetry coil 13 in the IPG 100 is demodulated (decoded) by the receiver circuit 458 in the IPG's data telemetry circuitry 459, and is sent to the IPG's microcontroller 452 for processing.

To save power, microcontroller 452 in the IPG 100 only periodically enables receiver circuitry 458 to "listen" for relevant data telemetry sent by the external controller 210. Such intermittent operation of receiver circuitry 458 consumes only a fraction of the power that would be consumed if the receiver circuit were to be kept continuously enabled. Thus, receiver circuitry 458 may listen for transmissions from the external controller 210 for a few milliseconds every second. During this listening window, the microcontroller 452 decodes any received data and compares it with a wake-up code stored in memory. If the received data does not match the wake-up code, the microcontroller 452 continues to only periodically enable receiver circuitry 458. Once a valid wake-up code is received from the external controller 210, microcontroller 452 can enable the transmitter circuitry 454 and the receiver circuitry 458 for continuous operation. Once data telemetry is completed, IPG 100 may receive a sleep code informing the microcontroller 452 to disable the transmitter circuitry 454 and revert the receiver circuitry 458 to periodic "listen" state.

Data telemetry from the IPG 100 to the external controller 210 occurs in much the same way. Data is modulated at transmitter circuitry 454, where it is FSK encoded. The data telemetry coil 13 broadcasts the FSK modulated magnetic field as data 480 or 488, which is picked up by either the data telemetry coil 217 or the charging coil 250 in the external controller 210. From there, the received data is demodulated at receiver circuitry 408 and sent to microcontroller 402 in the external controller 210 for processing. The microcontroller 402 can comprise a Texas Instruments' MSP430 microcontroller for example.

For transmitting power to the IPG 100, external controller 210 includes charging field generation circuitry 410 coupled to the charging coil 250, which circuitry 410 comprises a portion of charging circuitry 421. The charging field generation circuitry 410 generates a non-modulated alternating current that flows through the charging coil 250, which generates a magnetic charging field 484 that induces an alternating current in coil 18 in the IPG 100. Rectifier 460 converts the induced alternating current into DC voltage that is fed to the battery 296 via a charging and protection circuit 462 that monitors and controls the battery 269 charging process. Charging and protection circuit 462 can communicate status of the battery 296 to the microcontroller 452, which may use the data as an input to a power management program. Usually all circuitry within the IPG 100 draws power from the battery 296, but this is not strictly necessary. The frequency of the non-modulated magnetic charging field 484 is typically different from the frequency of the data telemetry fields 480 or 488. For example, while FSK data 480 or 488 can be approximately 125 kHz as noted earlier, the charging field 484 can be approximately 80 kHz. However, the use of different frequencies for data telemetry and for charging is not required in all useful applications of the disclosed techniques; the two frequencies can be the same.

During charging, i.e., when the external controller 210 is producing the magnetic charging field 484, the IPG 100 can communicate data 486 back to the external controller using Load Shift Keying (LSK). LSK modulator 470 receives data to be transmitted back to the external controller 210 from the IPG's microcontroller 452. The LSK modulator 470 uses that data to modulate the impedance of the charging coil 18. In one example, the impedance is modulated via control of a load transistor 472, with the transistor's on-resistance providing the necessary modulation. This change in impedance is reflected back to coil 250 in the external controller 210, where it is decoded using LSK receiver circuitry 420 within the charging circuitry 421. As noted earlier, LSK data 486 can only be communicated when the magnetic charging field 484 is present, and can only comprise a one-way communication from the IPG 100 to the external controller 210.

Because charging coil 250 can be used for charging as well as data telemetry in accordance with embodiments of the invention, the charging coil 250 can be connected to either the charging circuitry 421 or the data telemetry circuitry 409. Moreover, data telemetry can either occur through the regular data telemetry coil 217 or through the charging coil 250, and so the data telemetry circuitry 409 can be coupled to both of these coils.

Establishing such connections at appropriate times is accomplished by switches 430 and 431, which are respectively controlled by control signals K1 and K2 issuing from the microcontroller 402. When the charging coil 250 is to be used for charging, i.e., for producing power 484, switch 431 couples the charge coil 250 to the charging circuitry 421; switch 430 is left open. When the data telemetry coil 217 is to be used for data telemetry in a manner not overlapping with a charging session, i.e., for transmitting or receiving data 480, switch 430 connects the data telemetry coil 217 to the data telemetry circuitry 409; switch 431 can be left open or can couple the charging coil 250 to the charging circuitry 421. When the charging coil 250 is to be used for data telemetry when a charging session has already been initiated, i.e., for transmitting or receiving data 488, switch 430 connects the charging coil 250 to the data telemetry circuitry 409; switch 431 is left open to decouple the charging coil 250 from the charging circuitry 421.

Because charging (484) and data telemetry (480/488) can be carried out at different frequencies—for example 80 kHz and 125 kHz in the disclosed examples—it is advantageous to tune the charging coil 250 to either of these frequencies depending on whether the charging coil 250 is presently being used for charging or for data telemetry. Such tuning can occur using switch 432, which is controlled by control signal K3, also issued by the microcontroller 402. When the charging coil 250 is used for data telemetry, switch 432 is opened, and the tank circuit formed by capacitor 524 and the inductance of coil 250 tunes resonance at the higher data telemetry frequency. By contrast, during charging, switch 432 is closed. This includes auxiliary capacitor 544 into the tank circuit, which tunes the resonance to the lower frequency level. Alternatively, a variable capacitor can be used in lieu of capacitors 524 and 544 to set the resonance of the tank circuit. (It should be remembered that tuning to different frequencies is optional, and need not occur if data telemetry and charging occur at the same frequencies; in that case, switch 432 and capacitor 544 can be dispensed with).

The following chart summarizes the various modes of communication, and the setting of the switches (assuming that different frequencies are used for data telemetry and charging):

| Mode | Switch 430 | Switch 431 | Switch 432 |
|---|---|---|---|
| data telemetry via data telemetry coil (480) | coupled to data telemetry coil 217 | don't care | don't care |

-continued

| Mode | Switch 430 | Switch 431 | Switch 432 |
|---|---|---|---|
| data telemetry via charging Coil (488) | coupled to charging coil 250 | open | open |
| charging (484) | open | coupled to charging coil 250 | closed |

Switches 430, 431, and 432 can be of the electro-mechanical relay type or can be made of solid state devices. Control signals K1, K2, and K3 are shown as single control signals, but may in fact comprise a bus of control signals. Having more than one control signal can be especially beneficial to control switches (e.g., 430) having more than two possible positions.

Figure 6:
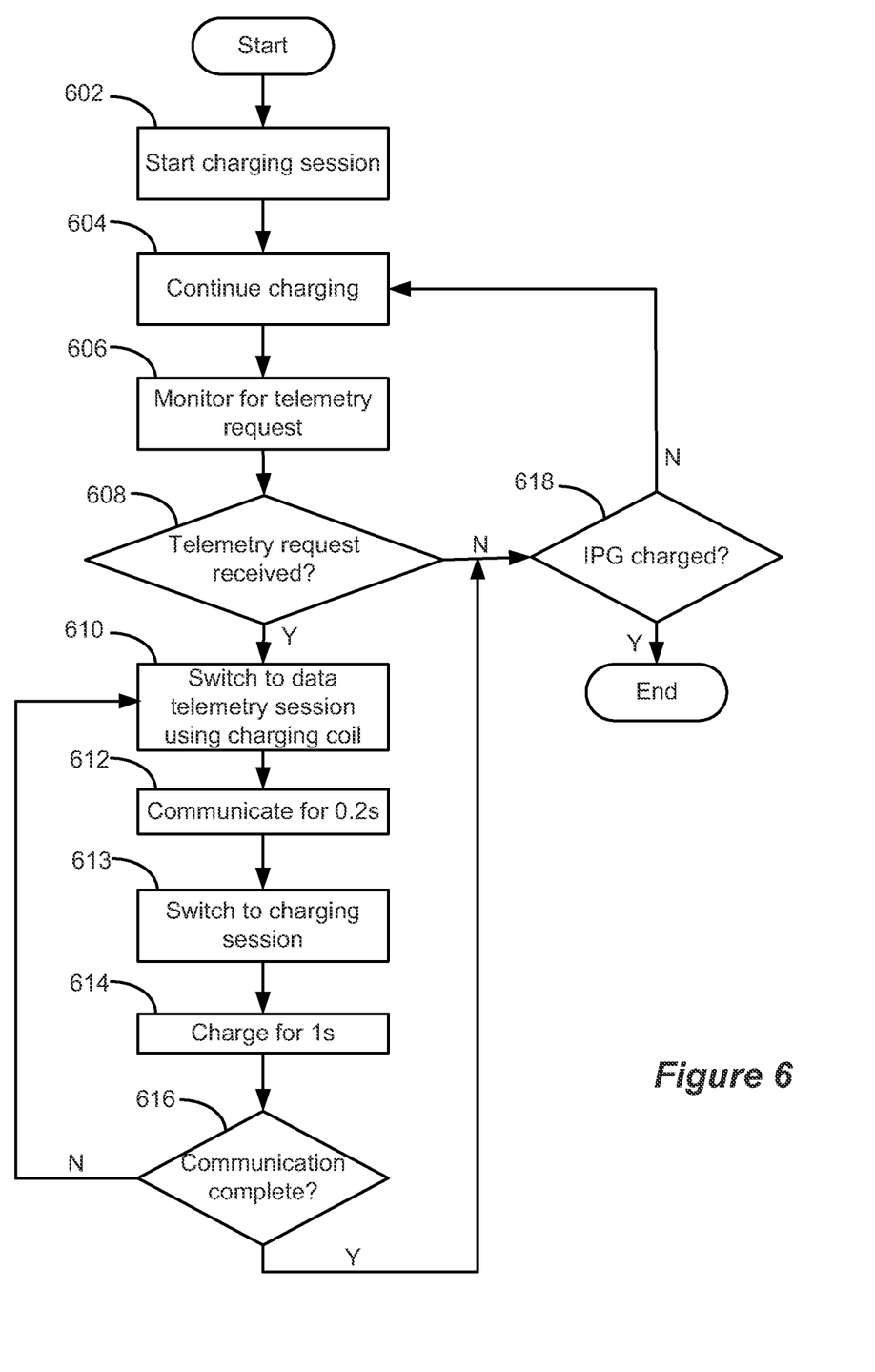
FIG. 6 shows a method of performing data telemetry using the charging coil in accordance with an embodiment of the invention in which telemetry and charging are interleaved.
Figure 7:
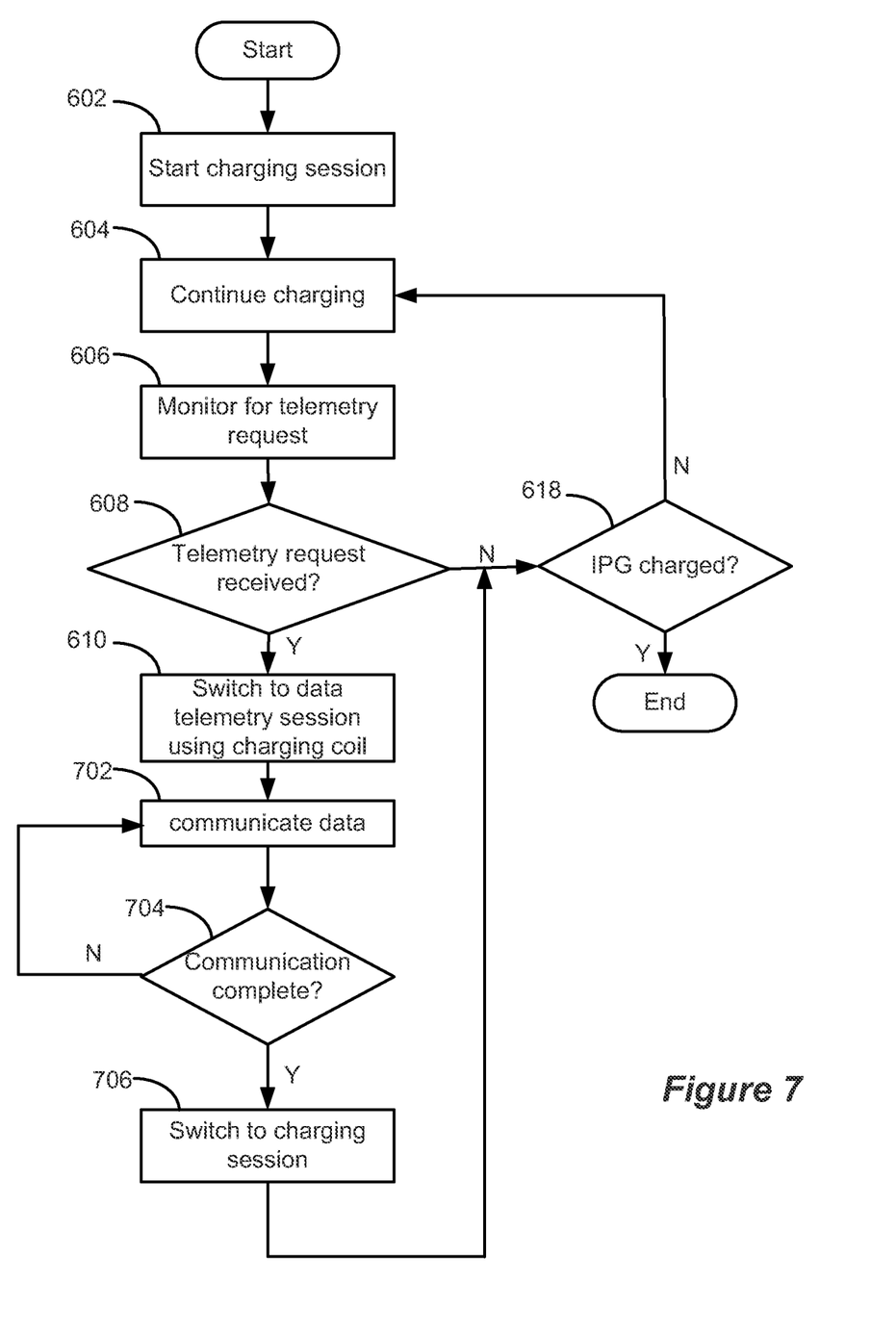
FIG. 7 shows a method of performing data telemetry using the charging coil by interrupting charging until data telemetry is completed in accordance with an embodiment of the invention.

With the communication circuitry explained, attention can turn to exemplary methods in which the external controller/charger system 200 can be used, and FIGS. 6 and 7 illustrate two such methods. In both methods, it is assumed that a charging session is underway, and that telemetry is requested during that session. Such a telemetry request can be a user request, for example, a patient who during charging uses the user interface of the external controller 210 to adjust the therapy current being delivered by the IPG. The telemetry request can also be one automatically activated by the software in the external controller to update IPG software or query the IPG's status for example. In either case, charging and data telemetry are time domain multiplexed, such that the external controller 210, and charging coil 250, are dedicated to either the data telemetry or charging session at any given point in time. In FIG. 6, the data telemetry session interrupts the charging session by interleaving data telemetry and charging, while in FIG. 7 the data telemetry session interrupts the charging session until data telemetry is wholly complete, and the then the charging session is resumed.

In FIG. 6, the external controller 210 begins a charging session at step 602: external charging coil 250 is energized by the charging circuit 410 to produce power 484, and the switches are set appropriate as noted in the above chart. To review, the charging coil is decoupled from the data telemetry circuitry 409, and is tuned to 80 kHz if necessary, e.g., if different frequencies are used for data telemetry and charging. In step 604, the external controller 210 continues charging IPG 100. In step 606, external controller 210 monitors for telemetry requests, which again may be user initiated or automatic generated. If no such request is received (step 608), the process repeats until the IPG is charged (step 618).

If a telemetry request is received (step 608), external controller 210 switches to a data telemetry session (step 610) in which data telemetry occurs through the charging coil 250. As noted earlier, because charging had been occurring in earlier steps, it can be assumed that alignment between the charging coil 250 and the IPG 100 is acceptable, and thus data telemetry through the charging coil 250 can begin automatically and without the need for physical realignment. As set forth in the above table, the charging coil 250 is now coupled to data telemetry circuitry 409 via switch 430 and decoupled from the charging circuitry 421 via switch 421, and switch 432 is opened to retune resonance of the tank circuitry to the data telemetry (FSK) frequency of 125 kHz. (Again, such retuning is optional and is unnecessary if data telemetry and charging occur at the same frequency).

With the circuitry so configured, FSK data telemetry can occur between the charging coil 250 and the telemetry coil 13 in the IPG 100 (step 612). As noted earlier, such telemetry begins by telemetry circuit 409 continuously broadcasting a wake-up code to IPG 100. Once IPG 100 detects a valid wake-up code, it sends an acknowledgement to the external controller 210 indicating that IPG 100 is ready to carry out data telemetry. External controller 210 then, according to the method of FIG. 6, starts a data telemetry timer specifying a maximum length of time for the data telemetry session. The data telemetry timer might be 0.2 seconds for example, but could of course vary depending on designer preferences. Prior to expiration of the timer, external controller 210 sends a sleep code to the IPG 100, even if not all data has yet been telemetered. Upon receiving the sleep code, IPG 100 goes back to periodically listening for wake-up code from the external controller 210.

Thereafter, in step 613, the external controller 210 once again automatically reconfigures its communication circuitry to perform a charging session, and the switches are appropriately controlled to reconnect the charging coil 250 with the charging circuitry 421, and to retune the charging coil to the charging frequency if necessary (e.g., 80 kHz). A charging timer is then started (614), for example, a 1 second timer, and the charging session continues for that period. (Note that during charging the IPG 100 can communicate data back to the external controller 210 using LSK modulator 470, as occurred in the prior art). After the charging timer expires, the status of data telemetry is determined in step 616. If the external controller 210 needs additional time to complete the data telemetry operation that was previously started (step 612), external controller 210 switches back to data telemetry (step 610). Thus, data telemetry sessions and charging sessions are interleaved through the repetition of steps 610-616. Eventually, when the data telemetry session is complete (step 616), the method can return to the charging session (step 604) until another telemetry request is received (step 608) or until charging is complete (step 618). Once charging is complete, the user may wish to disconnect the external charging coil assembly 220 from external controller 210.

In the method of FIG. 7, data telemetry and charging through the charging coil 250 are not interleaved as in FIG. 6. Instead, when a data telemetry session is indicated, the charging session is automatically suspended until the data telemetry session is completed, at which time the charging session is once again automatically. Such different steps are shown in FIG. 7 at steps 702-706. This alternative method may be sensible to implement in situations where the data telemetry is minimal, or will only take a small amount of time. In such circumstances, convenience dictates simply completing the telemetry rather than alternating the communication circuitry between data telemetry and charging.

Although the disclosed techniques are illustrated as being particularly useful when implemented in an integrated external controller/charger system 200 as illustrated in FIG. 3, it should be noted that the techniques are not limited to this particular hardware. For example, the disclose techniques can be implemented in an external device having a single housing containing both the data telemetry and charging coils, such as that illustrated in U.S. Pat. No. 8,335,569, which is incorporated herein by reference.

Figure 8:
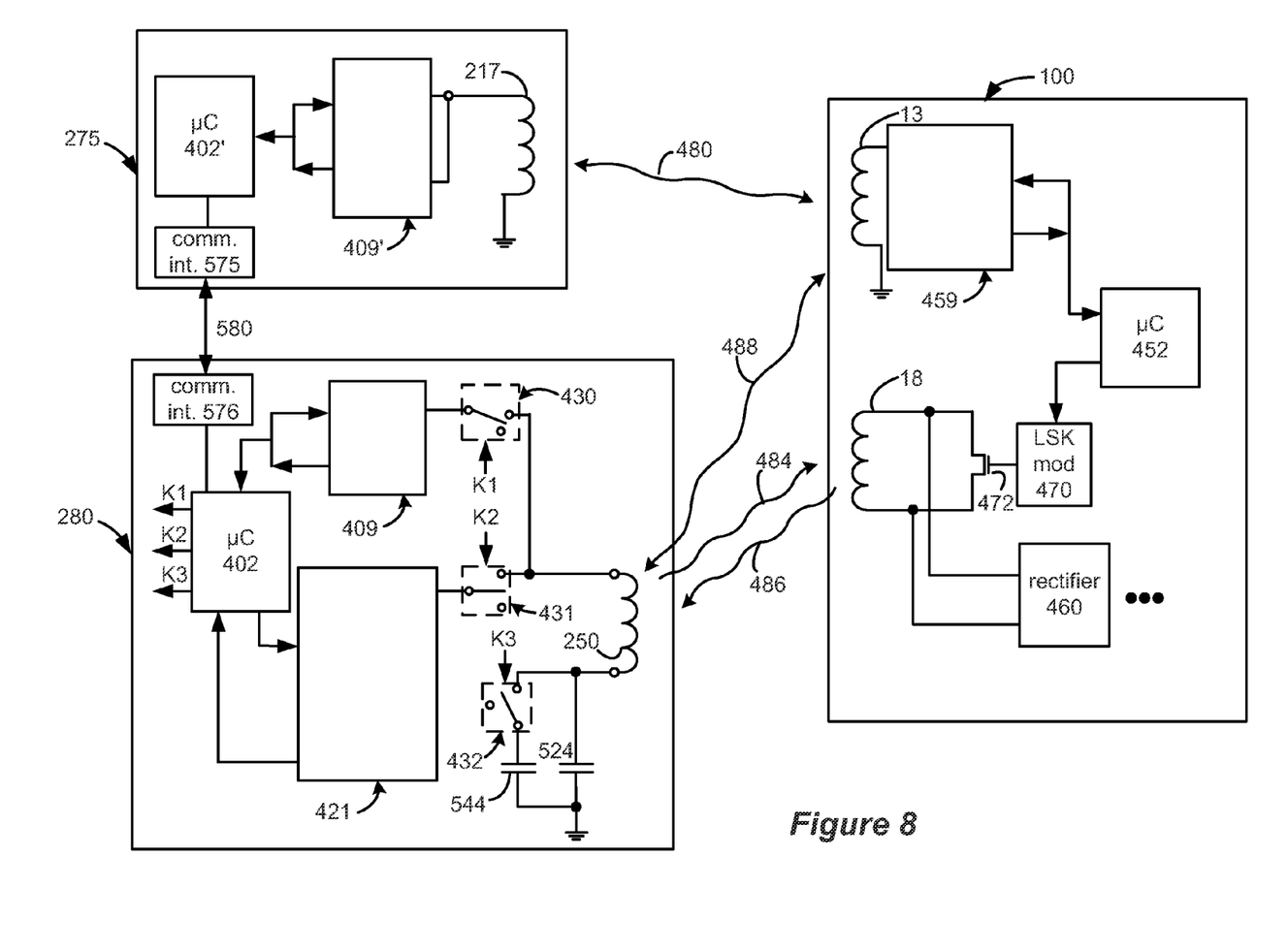
FIG. 8 shows a schematic of the circuitry within an external controller, a separate external charger, and the IPG in accordance with another embodiment of the invention.

The disclosed technique can also be implemented in system similar to that illustrated in FIG. 2 having separate and independently-functioning external controllers and external chargers. This alternative is illustrated in FIG. 8, which shows schematics for an external controller 275 and a separate external charger 280. Although these external devices 275 and 280 are separate, they together retain the same functionality as system 200 illustrated earlier, and thus many of the element numerals are retained to the extent they are similar. External controller 275 provides FSK data 480 with the telemetry coil 13 in the IPG 100, as in the prior art. External controller 280, which in this example includes an internal charging coil 250, provides power 480 to the charging coil 18 in the IPG 100, again as in the prior art. However, the external charger 250 also contains data telemetry circuitry 409, similar or identical to the data telemetry circuitry 409' provided in the external controller 275, and therefore the external charger 280 via charging coil 250 can either transmit data 488 with the IPG's data telemetry coil 13, or can provide power to the IPG's charging coil 18. Again, switches 430-432 are provided to isolate the data telemetry and charging circuits from each other, and to tune the charging coil 250 to a data telemetry or charging frequencies.

Whether the external charger 280 will conduct a data telemetry session or a charging session will depend on information received from the external controller 275 via communication link 580. As shown, this communication link 580 is supported by communication interface circuitry 575 and 576 in the controller 275 and charger 280 respectively. Link 580 can be wireless, for example a short-range directionless Bluetooth or WiFi link, or can comprise a wired connection coupling to data ports (not shown) on each of the devices 275 and 280.

Regardless, external charger 280 and external controller 275 can inform each other regarding status, and can take appropriate action. For example, if the external controller 275 understands that external charger 280 is currently involved in a charging session, and if the external controller 275 receives a telemetry request, the external controller 275 can provide the data to be telemetered to the external charger 280 via link 580. The external charger 280 in turn can suspend the charging session, and provide the data 488 to the data telemetry coil 13 in the IPG via charging coil 250 in the external charger pursuant to the methods illustrated earlier. As before, this requires the microcontroller 402 in the external charger 280 to issue control signals to close switch 430 to couple the charging coil 250 to the data telemetry circuitry 409; to open switch 431 to decouple the charging coil 250 from the charging circuitry 421; and to open 432 to properly tune the charging coil to the data telemetry frequency (e.g., 125 kHz). Once data telemetry is complete, the external charger 280 can notify the external controller 275 via link 580, and reset the switches as appropriate to continue the charging session. As with system 200 discussed earlier, such means of data transmission occurs via the external charger 280/charging coil 250 automatically, perhaps unbeknownst to a patient that might be interfacing with the external controller 275 to perform a data telemetry function.

"Coil" as used herein need not comprise windings, and instead can comprise any type of radiator or antenna more generally. Additionally, it should be understood that a coil performing a function can include one or more coils for performing that function. Although the implant as shown herein contains a data telemetry coil and a charging coil, it should be understood that this is not strictly required in implementation of the disclosed techniques. For example, the technique can be employed in implementations in which the implant contains only a single coil for performing both data telemetry and charging, such as is disclosed in U.S. Pat. No. 6,631,296. A frequency can comprise a band or range of frequencies, as should be clear from context.

Although particular embodiments of the present invention have been shown and described, it should be understood that the above discussion is not intended to limit the present invention to these embodiments. It will be obvious to those skilled in the art that various changes and modifications may be made without departing from the spirit and scope of the present invention. Thus, the present invention is intended to cover alternatives, modifications, and equivalents that may fall within the spirit and scope of the present invention as defined by the claims.

What is claimed is:

1. A method for communicating with an implantable medical device using an external system, comprising:
   providing power to the implantable medical device from a first coil during a charging session, wherein the first coil is external to and coupled to a hand-holdable housing;
   receiving a data telemetry request at a user interface of the housing to transmit first data to adjust a therapy being provided by the implantable medical device;
   interrupting the charging session to transmit at least a portion of the first data through the first coil during a first data telemetry session; and
   transmitting second data during a second data telemetry session through a second coil in the housing when a charging session is not occurring.

2. The method of claim 1, wherein the data telemetry request results from a patient's interaction with the user interface.

3. The method of claim 1, wherein interrupting the charging session comprises conducting the entire data telemetry session, and then resuming the charging session.

4. The method of claim 1, wherein interrupting the charging session comprises interleaving the data telemetry session and the charging session.

5. The method of claim 1, wherein the first coil is tuned to a first frequency during the charging session and is tuned to a second frequency when conducting the at least a portion of the data telemetry session.

6. The method of claim 5, wherein the second coil is tuned to the second frequency when conducting the second data telemetry session.

7. The method of claim 1, wherein the first coil provides power at a first frequency and transmits the first data at a second frequency.

8. The method of claim 7, wherein the second coil transmits the second data at the second frequency.

9. The method of claim 1, wherein the first coil is coupled to the housing by a cable.

10. The method of claim 1, wherein the second data adjusts a therapy being provided by the implantable medical device.

11. The method of claim 10, wherein transmitting the second data occurs in response to receiving a data telemetry request at the user interface of the housing.

* * * * *